(12) United States Patent
Mangiardi

(10) Patent No.: US 8,706,198 B2
(45) Date of Patent: Apr. 22, 2014

(54) OPACITY TECHNOLOGY

(75) Inventor: Eric K. Mangiardi, Charlotte, NC (US)

(73) Assignee: Quali-Med GmbH, Winsen (Luhe) (DE)

( * ) Notice: Subject to any disclaimer, the term of this patent is extended or adjusted under 35 U.S.C. 154(b) by 298 days.

(21) Appl. No.: 13/173,414

(22) Filed: Jun. 30, 2011

(65) Prior Publication Data

US 2012/0010503 A1  Jan. 12, 2012

Related U.S. Application Data

(60) Provisional application No. 61/344,355, filed on Jul. 6, 2010, provisional application No. 61/344,543, filed on Aug. 17, 2010.

(51) Int. Cl.
| | | |
|---|---|---|
| A61B 6/00 | (2006.01) | |
| A61M 25/01 | (2006.01) | |
| A61M 25/10 | (2013.01) | |
| A61M 5/00 | (2006.01) | |
| A61B 19/00 | (2006.01) | |
| A61K 49/00 | (2006.01) | |
| A61K 49/04 | (2006.01) | |
| A61K 49/06 | (2006.01) | |
| A61K 49/22 | (2006.01) | |

(52) U.S. Cl.
CPC ........... *A61M 25/0108* (2013.01); *A61M 25/10* (2013.01); *A61M 5/007* (2013.01); *A61B 6/481* (2013.01); *A61B 2019/5454* (2013.01); *A61B 2019/5466* (2013.01); *A61M 2025/1079* (2013.01); *A61K 49/00* (2013.01); *A61K 49/04* (2013.01); *A61K 49/06* (2013.01); *A61K 49/22* (2013.01)
USPC ........... 600/431; 600/424; 600/433; 600/435; 604/82; 604/83; 604/85

(58) Field of Classification Search
None
See application file for complete search history.

(56) References Cited

U.S. PATENT DOCUMENTS

| | | | |
|---|---|---|---|
| 4,406,878 A * | 9/1983 | DeBoer | 424/9.451 |
| 5,221,485 A * | 6/1993 | Bosworth et al. | 210/651 |
| 5,450,847 A * | 9/1995 | Kampfe et al. | 600/420 |
| 5,592,940 A * | 1/1997 | Kampfe et al. | 600/431 |
| 6,984,373 B2 * | 1/2006 | Wescott et al. | 424/1.69 |
| 2003/0199971 A1* | 10/2003 | Tower et al. | 623/1.24 |
| 2004/0196735 A1* | 10/2004 | Barker et al. | 366/139 |
| 2004/0243055 A1 | 12/2004 | Tan | |
| 2005/0101860 A1 | 5/2005 | Patrick et al. | |
| 2006/0135959 A1* | 6/2006 | Yuan et al. | 606/83 |
| 2007/0191668 A1 | 8/2007 | Lubock et al. | |

FOREIGN PATENT DOCUMENTS

WO   2010026578 A1   3/2010

OTHER PUBLICATIONS

International Search Report and Written Opinion of the International Searching Authority, mailed Mar. 7, 2012 (Application No. PCT/US2011/042760, filed Jul. 1, 2011).

* cited by examiner

*Primary Examiner* — Long V. Le
*Assistant Examiner* — Bradley Impink
(74) *Attorney, Agent, or Firm* — Ping Wang; Andrews Kurth LLP

(57) ABSTRACT

A catheter device comprising a chamber containing an opacity enhancing substance is disclosed. The opacity enhancing substance is in a dried or semi-dried form within the chamber of the device. Release of a liquid into the chamber suspends the substance and forms an opacity enhancing solution that is released into the lumen of the device in order to enhance the opacity of the device for imaging.

10 Claims, 21 Drawing Sheets

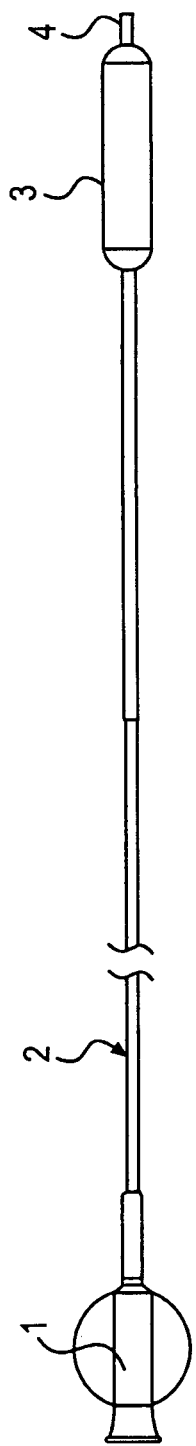
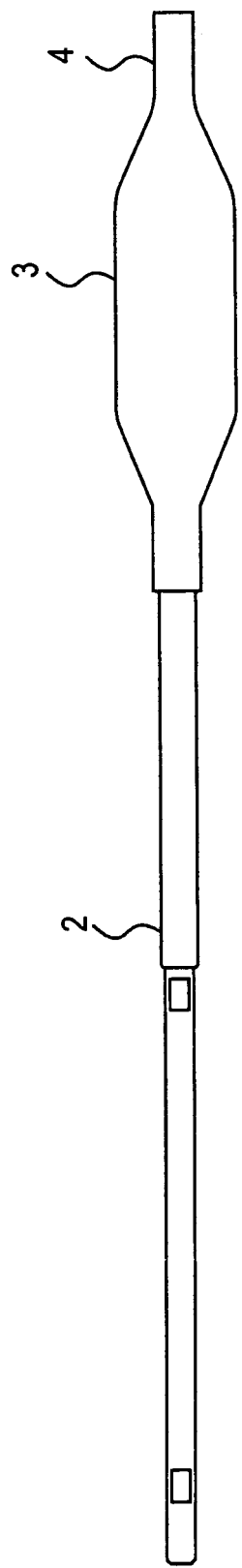
FIG. 1
FIG. 2

A.

B.

C.

D.

E.

F.

A.

B.

C.

D.

E.

OPACITY TECHNOLOGY

This application claims the priority from U.S. Provisional Patent Application Nos. 61/344,355, filed on Jul. 6, 2010, and 61/344,543, filed on Aug. 17, 2010. The entirety of all of the aforementioned applications is incorporated herein by reference.

FIELD

The present invention relates generally to medical devices and, in particular, to devices for introducing an opacity enhancing material into a medical catheter or hollow lumen devices, such as balloons.

BACKGROUND

Balloons and catheters are used throughout the body in various lumens such as vascular, neurovascular and non-vascular lumens or cavities. In order to give the devices some radio visibility during use, the devices may have material embedded in the distal tip or various marker positions.

In some cases, the devices are insufflated with various solutions to make the devices visible under fluoroscopy. The problem with using a solution-filled device is that the device may become sticky or stiff, or have increased deflation or inflation times, making the device difficult to work with or hindering the ability of the practitioner to control the device in vivo.

There is a need for catheter devices that have increased visibility in vivo for imaging devices, but that are insertable in a deflated state, such that they are easier to control and to work with.

SUMMARY

One aspect of the present invention relates to a catheter device comprising a elongated catheter body having a proximal end and distal end and a conduit within the catheter body; and a mixing chamber at the proximal end of the catheter body, wherein the mixing chamber has a first port for receiving a liquid and is in fluid communication with the conduit, wherein the mixing chamber is configured to allow an opacity enhancing substance in the mixing chamber to be suspended, dissolved or diluted with a liquid received from the input port to form an opacity enhancing liquid. When connected to a permeable catheter or balloon catheter, the mixing chamber can also be used to carry drugs that will be released at a treatment site through the permeable catheter or balloon catheter.

In an embodiment, the mixing chamber further comprises an opacity enhancing substance.

In a related embodiment, the opacity enhancing substance is in a dried, semidried or concentrated liquid form.

In another embodiment, the opacity enhancing substance is adhered to the inner surface of the chamber.

In another embodiment, the mixing chamber further comprises a membrane or screen that separate the mixing chamber into two or more sections.

In another embodiment, the catheter device further comprises a balloon at the distal end, wherein the balloon is in fluid communication with the mixing chamber through the conduit.

In another embodiment, the mixing chamber further comprises a second port for receiving the opacity enhancing substance.

In another embodiment, the mixing chamber is configured to create a turbulent flow to mix the opacity enhancing substance with the liquid.

In another embodiment, the opacity enhancing substance is selected from the group consisting of iodine compounds, barium sulfate, barium iridium, iron particles, tungsten, fluorescent dyes, gadolinium, and microbubbles.

In a related embodiment, the iodine compound is an ionic iodine compound or a non-ionic iodine compound.

In a related embodiment, the ionic iodine compound is selected from the group consisting of diatrizoic acid, metrizoic acid, ioglicic acid, or salts thereof.

In another related embodiment, the non-ionic iodine compound is selected from the group consisting of iopadimol, iohexol, ioxilan, iopromide, and iodixanol.

In another embodiment, the catheter is selected from the group consisting of balloon catheters, vascular catheters, cardiac catheters, arterial catheters, venous catheters, neurovascular catheters, intestinal catheters, esophageal catheters, urinary catheters, and Foley catheters.

In another related embodiment, the catheter device further comprises a stent at the distal end of the catheter body.

In another embodiment, the mixing chamber is configured to receive a removable and replaceable cartridge containing the opacity enhancing material.

In a related embodiment, the removable and replaceable cartridge further contains a drug, to be used with a permeable catheter or balloon catheter.

In another embodiment, the opacity enhancing material is contained in a pouch, packet, capsule or bag that is inserted into the mixing chamber through an aperture.

In another embodiment, the opacity enhancing material is contained in a tablet, pellet, pill, disc or wafer that is inserted into the mixing chamber through an aperture.

Another aspect of the present invention relates to a mixing device comprising a mixing chamber having a first port for connecting to a liquid delivery device, a second port for connecting to a catheter, and an opacity enhancing material inside the mixing chamber, wherein the mixing chamber is configured to allow the opacity enhancing substance to be suspended, dissolved or diluted with a liquid received from the input port to form an opacity enhancing liquid.

In one embodiment, the opacity enhancing substance is in a dried, semi-dried or concentrated liquid form.

In another embodiment, the opacity substance is adhered to the inner surface of the chamber.

In another embodiment, the mixing chamber further comprises a membrane or screen that separate the mixing chamber into two or more sections.

In another embodiment, the opacity enhancing material is contained in a removable and replaceable cartridge.

In another embodiment the mixing chamber further comprises a third port for receiving the opacity enhancing substance.

In another embodiment, the mixing chamber is configured to create a turbulent flow to mix the opacity enhancing substance with the liquid.

Another aspect of the present invention is a method of imaging a balloon catheter in a subject in need thereof, comprising the steps of: introducing into a lumen of the subject a balloon catheter device comprising a mixing chamber, wherein the mixing chamber is in fluid communication with the balloon catheter; admixing an opacity enhancing material with a liquid in the mixing chamber to form an opacity enhancing liquid, advancing the opacity enhancing liquid into the balloon catheter to inflate a balloon; and obtaining an image of the balloon in said subject.

In one embodiment, the opacity enhancing liquid further contains a therapeutic agent and the balloon catheter comprises a balloon that is permeable to the therapeutic agent.

The device and the method of the present invention may be used in procedures such angioplasty, angiography, balloon septostomy balloon sinuplasty, catheter ablation, administration of intravenous fluids, medication or parenteral nutrition with a peripheral venous catheter, drainage of fluid collections, e.g. an abdominal abscess, temporary blockage of a passage or lumen, expansion of a narrowed passage or lumen, expansion of a narrowing of the intestine, drainage of urine from the kidney by percutaneous nephrostomy, draining urine from the urinary bladder by urinary catheterization, and suprapubic catheterization.

Further objectives, features and advantages of the invention will be apparent from the following detailed description taken in conjunction with the accompanying drawings.

BRIEF DESCRIPTION OF THE DRAWINGS

For the purposes of this disclosure, unless otherwise indicated, identical reference numerals used in different figures refer to the same component.

FIG. 1 shows a representative view of a catheter with a balloon attached at a distal end.

FIG. 2 shows a representative view of a balloon attached to a catheter.

DETAILED DESCRIPTION

Figure 3:
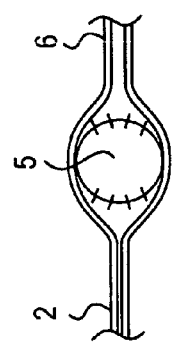
FIG. 3 is a perspective view of an embodiment of a mixing chamber.

While this invention may be embodied in many different forms, there are described in detail herein specific preferred embodiments of the invention. This description is an exemplification of the principles of the invention and is not intended to limit the invention to the particular embodiments illustrated.

The present invention provides a device that provides visibility/opacity of the device that allows the practitioner to see the device under imaging wherein the visibility/opacity substance could be free floating inside the device in a dried or semi-dried state that becomes active when a pharmaceutically acceptable solution is introduced into the device and mixed with the substance. Various catheter devices or hollow lumen structures are disclosed, wherein an opacity enhancing substance can be adhered to the inner lumen of the device or structure or positioned into the inner lumen as part of the application during or after the manufacturing process. In certain embodiments, the opacity enhancing substance is positioned loosely or fixed into a natural indentation, crevasse, hole, or other modulus that will allow the opacity enhancing substance to be attached to the inner lumen of the device or to be loosely adhered or fixed with a quick biodegradable technology that will allow the material to be suspended, activated or dissolved in the lumen of the catheter or the balloon using a pharmaceutically acceptable carrier to allow the lumen and or balloon end of the catheter to have increased visibility under imaging devices. When connected to a permeable catheter or balloon catheter, the mixing chamber can also be used to carry drugs that will be released at a treatment site through the permeable catheter or balloon catheter.

Examples of a "dried" state of the opacity substance include, but are not limited to a powder, granular, solid, cake, tablet or crystalline form. Examples of a "semi-dried," or semi-liquid, state of the opacity substance include, but are not limited to a gel, slurry, paste, or a viscous liquid.

The terms "opacity enhancing substance," "opacity substance," and "visibility substance" refer to a medical contrast medium, or contrast agent, that increases or enhances the visibility of a medical device, such as a catheter or balloon, within the body of a subject for a medical imaging device or procedure. Exemplary opacity enhancing substances include, but are not limited to: iodine compounds, barium sulfate, barium iridium, iron particles, tungsten, fluorescent dyes, gadolinium, and microbubbles.

Iodine compounds can be ionic (high osmolar) or non-ionic (low osmolar) compounds. Exemplary ionic iodine compounds may comprise diatrizoic acid, metrizoic acid, ioglicic acid, or salts thereof. Exemplary non-ionic iodine compounds may comprise iopadimol, iohexol, ioxilan, iopromide, and iodixanol.

Microbubbles are bubbles composed of nitrogen or perfluorocarbon gas smaller than one millimeter in diameter, but larger than one micrometer encapsulated with a solid shell. The shell is made from a polymer, lipid or a protein such as serum albumin.

A medical imaging device or procedure is inclusive of any device or method used to locate, monitor or visualize a medical device, such as a catheter or balloon, within the body of a subject. Examples include, but are not limited to, X-ray, ultrasound, fluoroscopy, and magnetic resonance imaging.

A catheter is an elongated tube that can be inserted into a body cavity, lumen, duct, or vessel. The process of inserting a catheter is catheterization. In some uses, a catheter comprises a thin, flexible tube, or soft catheter. In other uses, it comprises a larger, solid tube, or hard catheter. A catheter left inside the body, either temporarily or permanently, may be referred to as an indwelling catheter. A permanently inserted catheter may be referred to as a permcath.

Catheter devices which are useful in the present invention include all types of balloon catheters. A balloon catheter is a type of soft, flexible catheter with an inflatable balloon at its tip which is used during a catheterization procedure to enlarge a narrow opening or passage within the body or to hold the catheter in place in a lumen during a procedure. The deflated balloon catheter is positioned, then inflated to perform the necessary procedure, and deflated again in order to be removed. In some embodiments, the balloon catheter may comprise a stent, which is located around the balloon, expands when the balloon is inflated, and remains in place when the balloon is deflated. Types of catheters useful in the present invention include, but are not limited to, vascular catheters, including cardiac catheters, arterial catheters, and venous catheters; neurovascular catheters; intestinal catheters; esophageal catheters and urinary catheters, such as Foley catheters.

Exemplary in vivo uses of a catheter of the present invention include, but are not limited to, angioplasty, angiography, balloon septostomy, balloon sinuplasty, catheter ablation, administration of intravenous fluids, medication or parenteral nutrition with a peripheral venous catheter, drainage of fluid collections, e.g. an abdominal abscess, temporary blockage of a passage or lumen, expansion of a narrowed passage or lumen, such as the intestine, drainage of urine from the kidney by percutaneous nephrostomy, draining urine from the urinary bladder as in urinary catheterization, e.g., the Foley catheter or even when the urethra is damaged as in suprapubic catheterization.

An exemplary catheter device with a balloon is depicted in FIG. 1. The device comprises a hub 1, an elongated catheter body 2 having at least one conduit therein, the balloon 3 and a distal tip 4. The length and diameter of the catheter body, the shape of the balloon and the volume of the balloon are dependent upon the application the balloon catheter is used for. An embodiment of the balloon and distal end of the catheter is provided in FIG. 2.

In the present invention, the hub can be modified to contain an opacity enhancing substance in a dry, semi-dry, gel or concentrated liquid form. The modified hub comprises a lumen or chamber for containing the substance. The liquid for inflating the balloon is introduced into the lumen or chamber, where it is mixed with the opacity enhancing substance. Suitable liquids for mixing with the opacity enhancing substance include any pharmacologically acceptable liquid, such as sterile water, saline, buffered solutions or any liquid known in the art as being suitable for the inflation of a balloon catheter. Subsequent to said mixing, the liquid enters into the catheter and inflates the balloon. Due to the presence of the opacity solution, the catheter and balloon are more visible for imaging.

For the present invention the hub of a balloon catheter can be modified to comprise a mixing chamber or lumen wherein the opacity enhancing substance is mixed with the liquid. In some embodiments, the mixing chamber or lumen is distal to the hub and is positioned in or proximal to the catheter (i.e., between the hub and the catheter). In still another embodiment, the invention contemplates that the mixing chamber or lumen is a separate article of manufacture that is attachable to the proximal end of the hub (i.e., the hub is between the mixing chamber and the catheter), wherein the liquid is introduced into the mixing chamber for mixing with the opacity enhancing substance, subsequently flowing through the hub into the catheter and inflating the balloon.

Some embodiments of the present device comprise a mesh, screen or membrane in the mixing chamber or as a component of a cylinder containing the opacity substance. In said embodiments, the pores or openings of the mesh, screen or membrane are sufficiently small to prevent the dried, semi-dried or gel opacity substance from passing through said pores or openings. However, said pores or openings allow the passage of liquid through the mesh, screen or membrane to admix with the opacity substance to form the opacity solution. Said pores or openings further allow the passage of the admixed opacity solution. In some embodiments, said pores or openings are of a uniform size. In other embodiments, said pores or openings are of differing sizes. In still other embodiments, said pores or openings may be larger on one side of the mixing chamber or cylinder and smaller on the other side of the mixing chamber or cylinder. In some embodiments, the said pores or openings of the mesh, screen or membrane create turbulence in the mixing chamber when the liquid is introduced to enhance the admixture with the opacity substance.

In some embodiments of the invention, the opacity substance is contained in a pouch, packet, capsule or bag that is a separate article of manufacture from the mixing chamber. Said pouch, packet, capsule or bag is inserted into the mixing chamber through an aperture. Said aperture is then closed with a cap being securely affixed into the mouth of the aperture by snap-fit, screw-fit or other adherent application. In a related embodiment, the pouch, packet, capsule or bag is made of a mesh or screen or membrane having pores or openings sufficiently small to prevent the dried, semi-dried or gel opacity substance from passing through said pores or openings. However, said pores or openings allow the passage of liquid through the mesh, screen or membrane to admix with the opacity substance to form the opacity solution. Said pores or openings further allow the passage of the admixed opacity solution out of the pouch, packet or bag. In another related embodiment, the pouch, packet, capsule or bag is made of a substance that is soluble in the liquid for inflating the balloon.

In another embodiment, the opacity substance is provided as a tablet, pellet, pill, disc or wafer that is a separate article of manufacture from the mixing chamber. The tablet, pellet, pill, disc or wafer is soluble in the liquid for inflating the balloon. Said tablet, pellet, pill, disc or wafer is inserted into the mixing chamber through an aperture. Said aperture is then closed with a cap being securely affixed into the mouth of the aperture by snap-fit, screw-fit or other adherent application.

The catheter device of the present invention may also be used for drug delivery to a treatment site. In one embodiment, the mixing chamber is connected to a catheter or balloon that is permeable to a therapeutic agent, and the therapeutic agent is added to the mixing chamber together with the opacity enhancing substance. The therapeutic agent may be in the form of a tablet, pellet, pill, disc or wafer. The therapeutic agent may be an antibiotic, an antimicrobial agent, an antiviral agent, an antibacterial agent, a thrombotic agent or a coagulant agent.

Mixing Chambers

The following are exemplary chambers for containing the opacity enhancing substance and mixing the substance with the liquid. The illustrations depicted and described are exemplifications of the concept for each of the types of chambers and are not intended to exactly show the shape or design of the chamber, nor to limit the scope of the disclosure to the exact shape or design shown in a drawing.

FIG. 3 shows an exemplary mixing chamber, which may be a modified hub, wherein a bulbous or rounded chamber 5 contains the opacity enhancing substance in a dried or semi-dried form. The liquid is introduced through the port 6, admixed with the opacity enhancing substance in the chamber 5, yielding an opacity solution that passes into and through the catheter 2 to inflate the distal balloon, allowing the balloon to be visualized during imaging.

Figure 4:
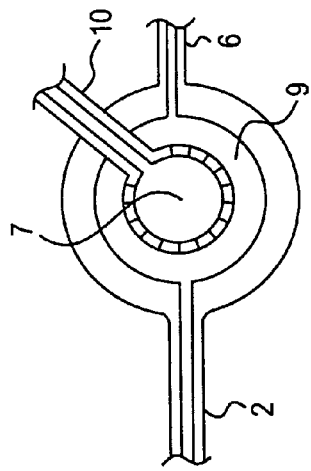
FIG. 4 shows a perspective view of another embodiment of a mixing chamber that contains a hollow canister for holding the opacity enhancing substance.

FIG. 4 shows another embodiment of a mixing chamber, wherein the opacity enhancing substance is retained in a cylinder 7. The cylinder 7 may be sealed within the chamber at the time of manufacture, or the cylinder 7 may be closed with a cap 8 that is securely affixed into the mouth of the cylinder 7 by snap-fit, screw-fit or other adherent application. Alternatively, the cylinder 7 is introduced into the mixing chamber 9 through an aperture and the aperture is then closed with cap 8 being securely affixed into the mouth of the aperture by snap-fit, screw-fit or other adherent application. One or more portions of the walls of the cylinder 7 are a screen or liquid permeable membrane or are perforated such that, when the liquid is introduced through the port 6, it enters the lumen 9 of the chamber, passes through the walls of the cylinder 7 and admixes with the opacity enhancing substance inside the cylinder 7. The opacity solution then passes into and through the catheter 2 to inflate the distal balloon, allowing the balloon to be visualized during imaging. FIGS. 26A-C depict an example of this embodiment as an article of manufacture, with FIGS. 27A-F also depicting an exemplary snap-fit embodiment of the cap for the device and its fitment into the mouth of the cylinder. In one embodiment, the cylinder 7 may further contain a drug, which can be delivered to a treatment site by a drug permeable catheter or balloon.

Figure 5:
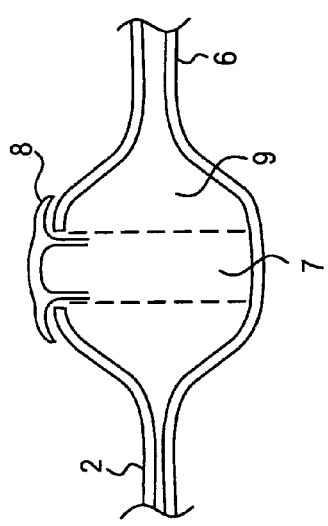
FIG. 5 is a perspective view of another embodiment of a mixing chamber.

FIG. 5 shows another design of the mixing chamber. This design allows the opacity enhancing substance to be introduced into the cylinder 7 through a port 10. Again, the liquid is introduced through port 6, enters the lumen 9 of the chamber, passes through the walls of the cylinder 7, admixes with the opacity enhancing substance and the opacity solution passes into and through the catheter 2 to inflate the distal balloon, allowing the balloon to be visualized during imaging.

Figure 6:
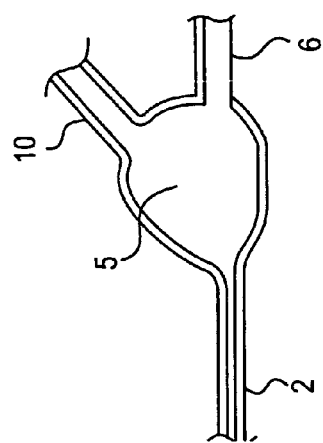
FIG. 6 is a perspective view of an embodiment of a mixing chamber with a two piece design.
Figure 7:
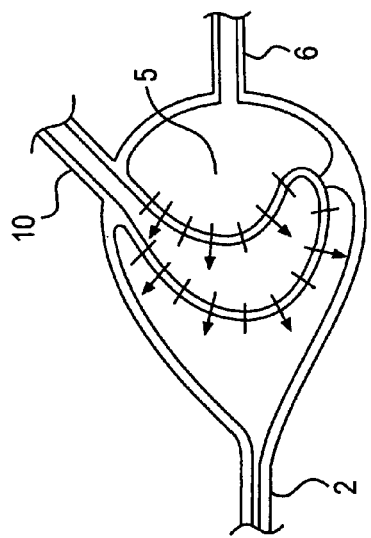
FIG. 7 is a perspective view of another embodiment of a mixing chamber with a two piece design.

FIGS. 6 and 7 show mixing chambers with a two-piece design, in which one of the two pieces is sealed during manufacture after the opacity enhancing substance is added. FIG. 6 contemplates a bulbous design for the chamber, while FIG. 7 contemplates a more conical shape, with the apex of the cone being oriented towards the catheter 2. These two piece chambers may further contain an additional port 10. The liquid is introduced through port 6, enters the chamber 5, and admixes with the opacity enhancing substance and the opacity solution passes into and through the catheter 2 to inflate the distal balloon, allowing the balloon to be visualized during imaging.

Figure 8:
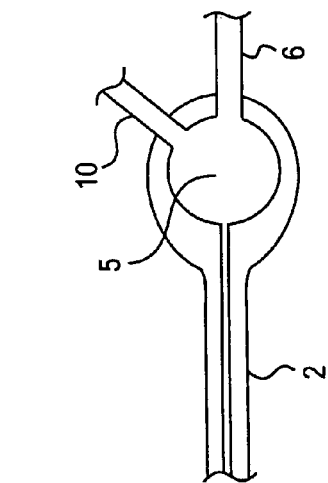
FIG. 8 is a perspective view of another embodiment of a mixing obundboc.

FIG. 8 shows another design of the mixing chamber. This design allows the opacity enhancing substance to be introduced into the chamber 5 through a port 10. The liquid is introduced through port 6, enters the chamber 5, and admixes with the opacity enhancing substance and the opacity solution passes into and through the catheter 2 to inflate the distal balloon, allowing the balloon to be visualized during imaging.

Figure 9:
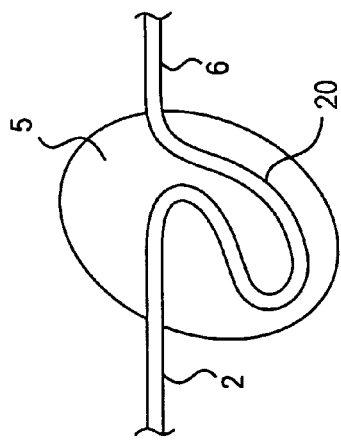
FIG. 9 is a perspective view of an embodiment of a mixing chamber designed to create a turbulent flow.

In certain instances, or with some opacity enhancing substances, it may be desirable to create additional turbulence within the chamber in order to more fully suspend or dissolve the opacity enhancing substance. An example of this concept is shown in FIG. 9, where the turbulence is resultant from the liquid introduced through port 6 flowing serpentine channel 20 in the chamber 5, where it admixes with the opacity enhancing substance adhered onto the surface of the channel 20. The opacity solution then passes into and through the catheter 2 to inflate the distal balloon, allowing the balloon to be visualized during imaging. In another embodiment, the turbulence can be caused by baffles incorporated into the chamber.

Figure 10:
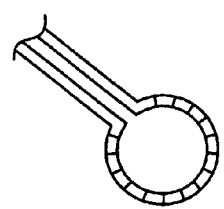
FIG. 10 is a perspective view of another embodiment of a mixing chamber.

FIG. 10 shows a perspective view of another variation of a chamber designed to create a turbulent flow.

Figure 11:
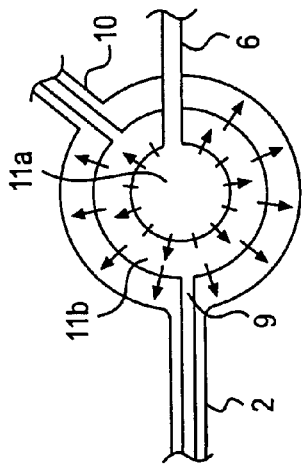
FIG. 11 is a perspective view of another embodiment of a mixing chamber.

In FIG. 11, the liquid is introduced through port 6 into a central lumen 11a, which is enclosed by a membrane or screen. The opacity enhancing substance is introduced through port 10 into a separate lumen 11b that surrounds lumen 11a and is also enclosed by a membrane or screen. The liquid flows from lumen 11a into lumen 11b, where it admixed with the opacity enhancing substance to form the opacity solution which flows into the lumen of the chamber 9 and passes into and through the catheter 2 to inflate the distal balloon, allowing the balloon to be visualized during imaging. In this embodiment, the screens or membranes create additional turbulence for the suspension or dissolution of the opacity enhancing substance.

Figure 12:
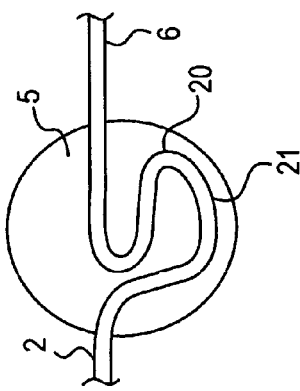
FIG. 12 is a perspective view of another embodiment of a mixing chamber designed to create a turbulent flow.

FIG. 12 provides another view of a turbulence design similar to FIG. 9. In this embodiment, the opacity enhancing substance 21 is adhered onto the surface of a section of the serpentine channel 20. The turbulent flow of the liquid through the channel 20 will suspend or dissolve the opacity enhancing substance 21, thereby forming the opacity enhancing substance.

Figure 13:
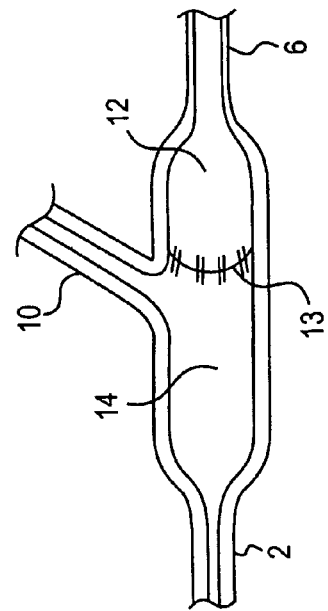
FIG. 13 is a perspective view of another embodiment of a mixing chamber designed to create a turbulent flow.

FIG. 13 depicts another exemplary chamber design wherein the increased turbulence is the result of flow through a membrane or screen. In this example, the opacity enhancing substance is introduced through port 10 into the mixing chamber 14. The liquid is introduced through port 6 into lumen 12, which is separated from the mixing chamber 14 by membrane 13. The liquid flows through membrane 13 into mixing chamber 14, where it admixed with the opacity enhancing substance to generate the opacity solution, which and passes into and through the catheter 2 to inflate the distal balloon, allowing the balloon to be visualized during imaging. In this embodiment, the screens or membranes create additional turbulence for the suspension or dissolution of the opacity enhancing substance.

Figure 14B:
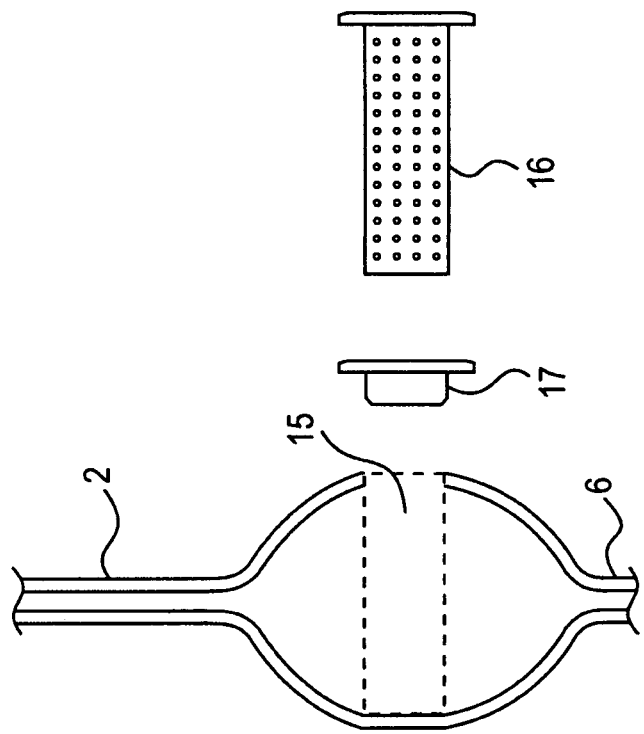
FIGS. 14A and 14B are perspective top view and side view, respectively, of another embodiment of a mixing chamber.
Figure 14A:
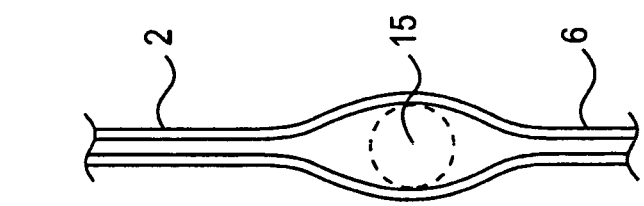

FIGS. 14A-B show a side view (A) and a top view (B) of a mixing chamber comprising an insertable canister 16 that contains an opacity enhancing substance. The canister 16 is loaded with the opacity enhancing substance and sealed with a cap 17 and inserted into the chamber 15. The walls of the canister 16 are a screen or membrane or are perforated such that, when the liquid is introduced through the port 6, it enters the lumen 15 of the chamber, passes through the walls of the canister 16, admixes with the opacity enhancing substance and the opacity solution passes into and through the catheter 2 to inflate the distal balloon, allowing the balloon to be visualized during imaging.

Figure 21A:
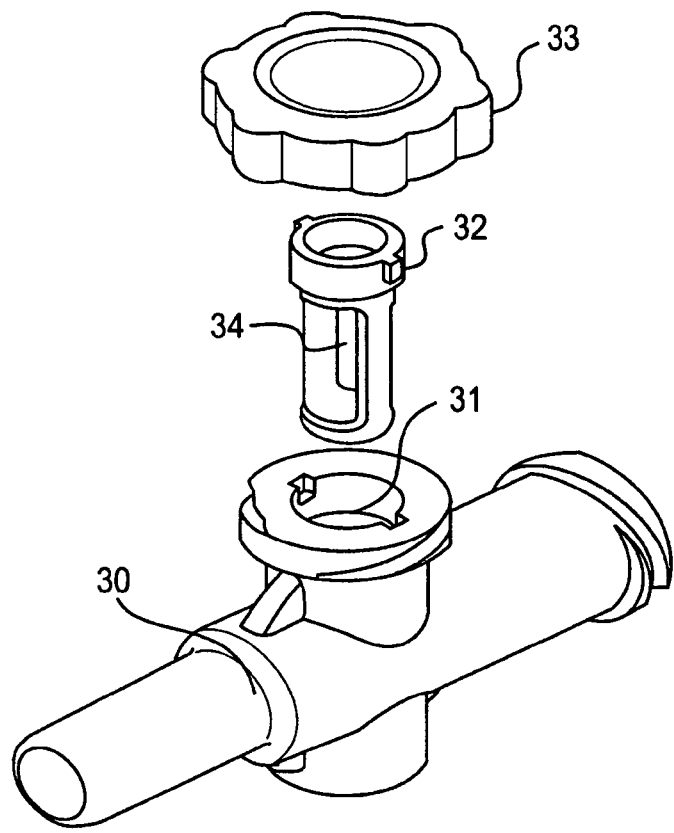
FIG. 21 shows a perspective drawing of an embodiment of the mixing chamber in an expanded view (A) of the body of the device comprising the mixing chamber, a cylinder for containing the opacity substance and a cap; as well as an assembled view of the device (B).

FIG. 21 depicts a rendering of an exemplary mixing chamber 30 of the invention. FIG. 21A is an exploded view of the components of the mixing chamber 30, which comprising a receptacle 31, a cylinder 32 for containing the opacity substance and a cap 33. The cylinder 32 comprises mesh 34 that holds the dried opacity substance, but allows liquid to pass into the cylinder 32, where it admixed with the opacity enhancing substance to generate the opacity solution, which and passes into and through the catheter to inflate the distal balloon, allowing the catheter and balloon to be visualized during imaging. In this embodiment, the mesh 34 creates additional turbulence for the suspension or dissolution of the opacity enhancing substance. Perspective view (B) depicts an assembled view of the mixing chamber 30. Cutaway drawings in the longitudinal horizontal (FIG. 22A) and transverse planes (FIG. 22B) through the mixing chamber 30 show exemplary dimensions of the device. An exemplary cylinder for containing the opacity substance, without the mesh, is depicted in FIG. 30A-C, while an example of mesh that can be incorporated into said cylinder is depicted in FIG. 31 A-C.

In some embodiments, the mixing chamber 30 is a separate article of manufacture from the catheter and can be attached to the hub of the catheter by way of a slip fitting, a Luer fitting, or a Luer lock fitting, for example. In an exemplary embodiment, FIG. 23 shows alternate perspective views (A & B) of a mixing chamber 30 of the present invention comprising a female Luer lock receptacle (36) at one end and a male Luer lock fitting (37) at the other end, with a central receptacle 35 for inserting a cylinder containing the opacity substance into the mixing chamber 30. FIGS. 28A-E provide additional depictions of this embodiment as an article of manufacture. FIGS. 29A-E depict an exemplary cap for the receptacle in the mixing chamber into which can be inserted a cylinder comprising the opacity substance. An exemplary cylinder for containing the opacity substance, without the mesh, is depicted in FIG. 30A-C, while an example of mesh that can be incorporated into said cylinder is depicted in FIG. 31 A-C.

Figure 24:
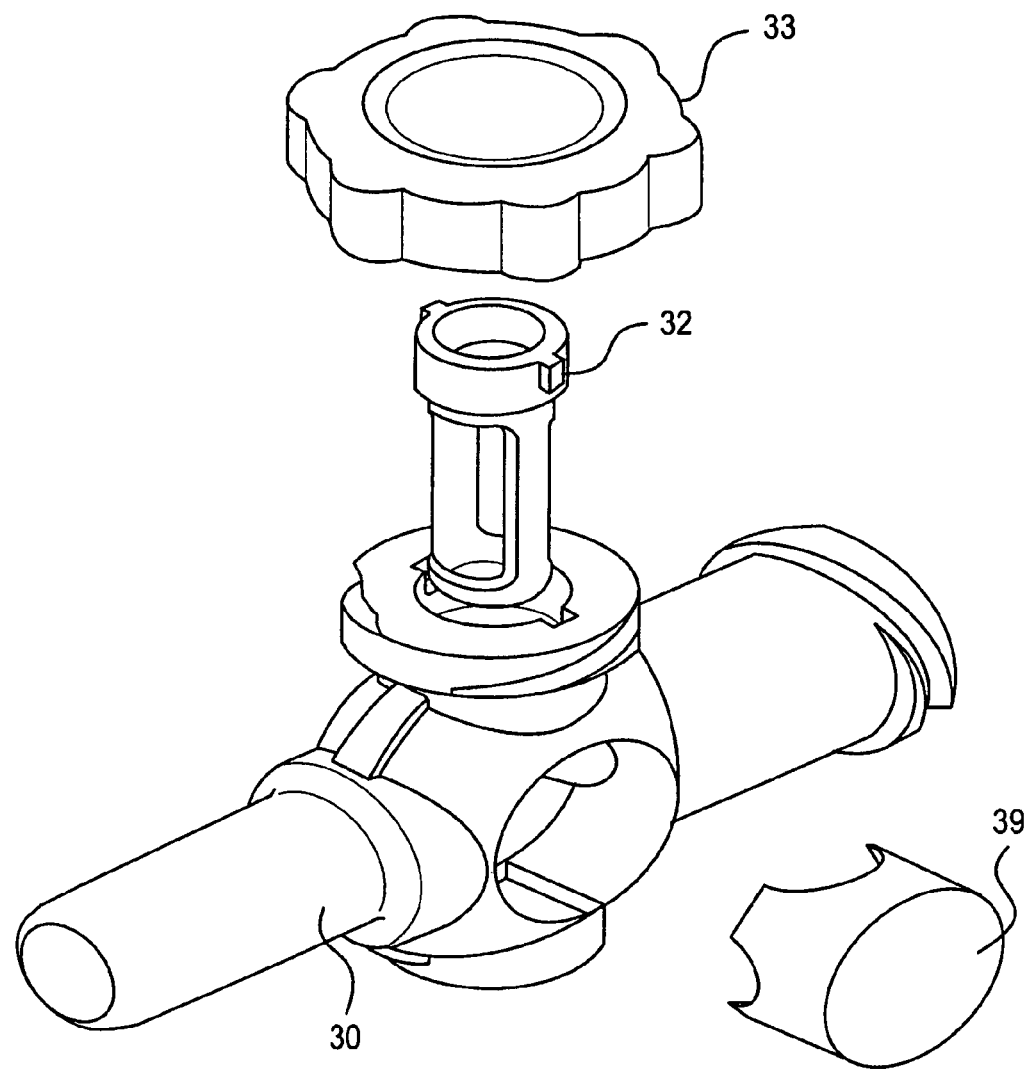
FIG. 24 shows an exploded view of a device of the present invention, having an interchangeable plug that fits into the side of the mixing chamber.

In some embodiments, the mixing chamber 30 can have at least one additional interchangeable element or plug 39 that forms part of the wall of the mixing chamber. This interchangeable element could be used, for example, to change the shape of the mixing chamber to modulate the turbulence of the mixing action when the liquid carrier is admixed with the opacity substance in the cylinder or mixing chamber. An exemplary, exploded view of such a device is depicted in FIG. 24. Cutaway drawings in the longitudinal horizontal (FIG. 25A) and transverse planes (FIG. 25B) through the mixing chamber show exemplary dimensions of the device measured in inches.

Control of Opacity

The intensity of the image and the level of opacity of the opacity solution in the catheter and balloon can be controlled by varying the amount of opacity enhancing substance used and the volume of liquid used to suspend or dissolve the opacity enhancing substance. In a preferred embodiment, the opacity enhancing substance is used in an amount large enough to allow an operator to visualize a medical device, such as a balloon catheter, inside the body using an imaging device, but small enough to allow the operator to see the anatomy through the image of the medical device.

Figure 15:
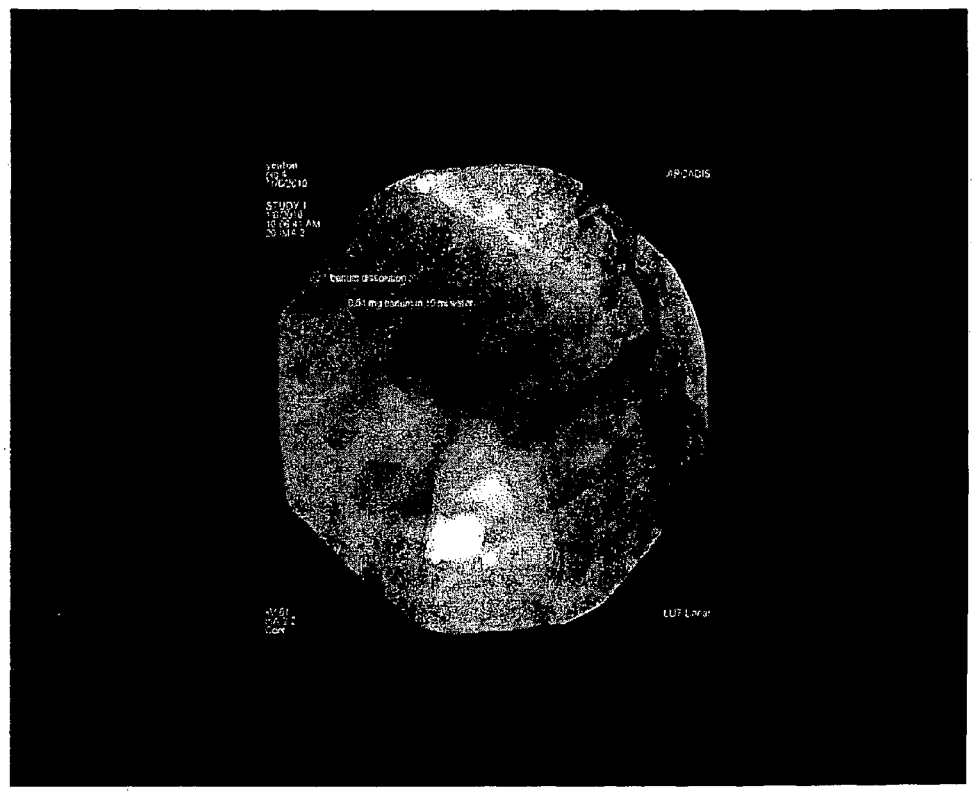
FIG. 15 shows an image of an esophageal balloon comprising a barium sulfate solution admixed at a concentration of 0.04 µg barium sulfate in 10 ml of sterile $H_2O$.

FIG. 15 shows an X-Ray image of an esophageal balloon comprising a barium sulfate solution admixed at a concentration of 0.04 µg barium sulfate in 10 ml of sterile $H_2O$, wherein the opacity of the balloon is not intense.

Figure 16:
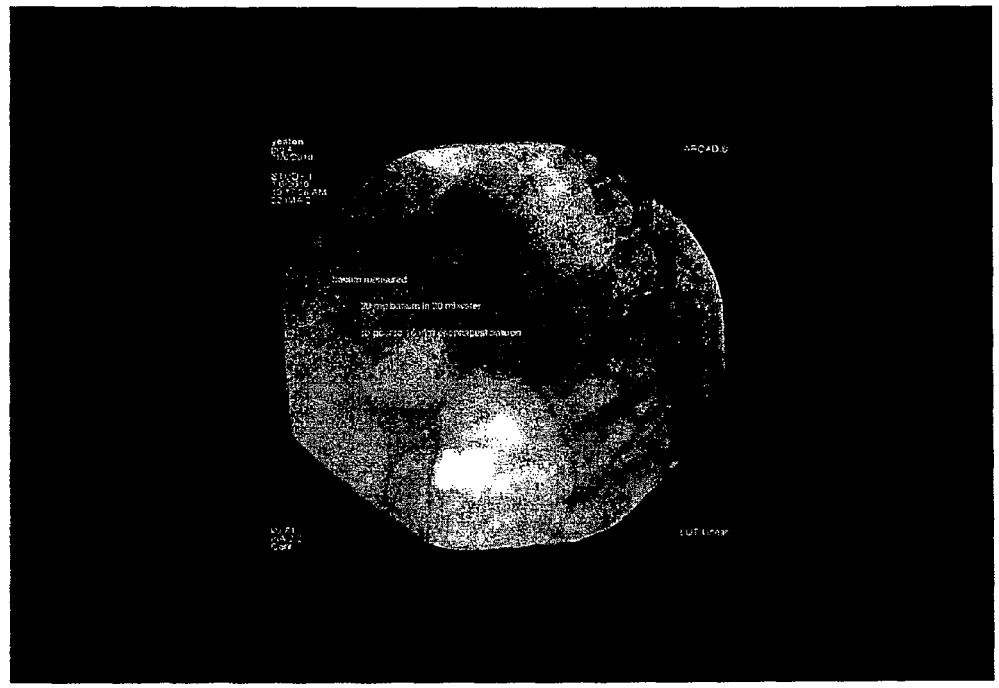
FIG. 16 shows an image of an esophageal balloon comprising a barium sulfate solution admixed at a concentration of 20 mg barium sulfate in 20 ml of sterile $H_2O$.

In FIG. 16, the X-Ray image of the esophageal balloon is more intense. In this example, the balloon comprises a barium sulfate solution admixed at a concentration of 20 mg barium sulfate in 20 ml of sterile $H_2O$.

Figure 17:
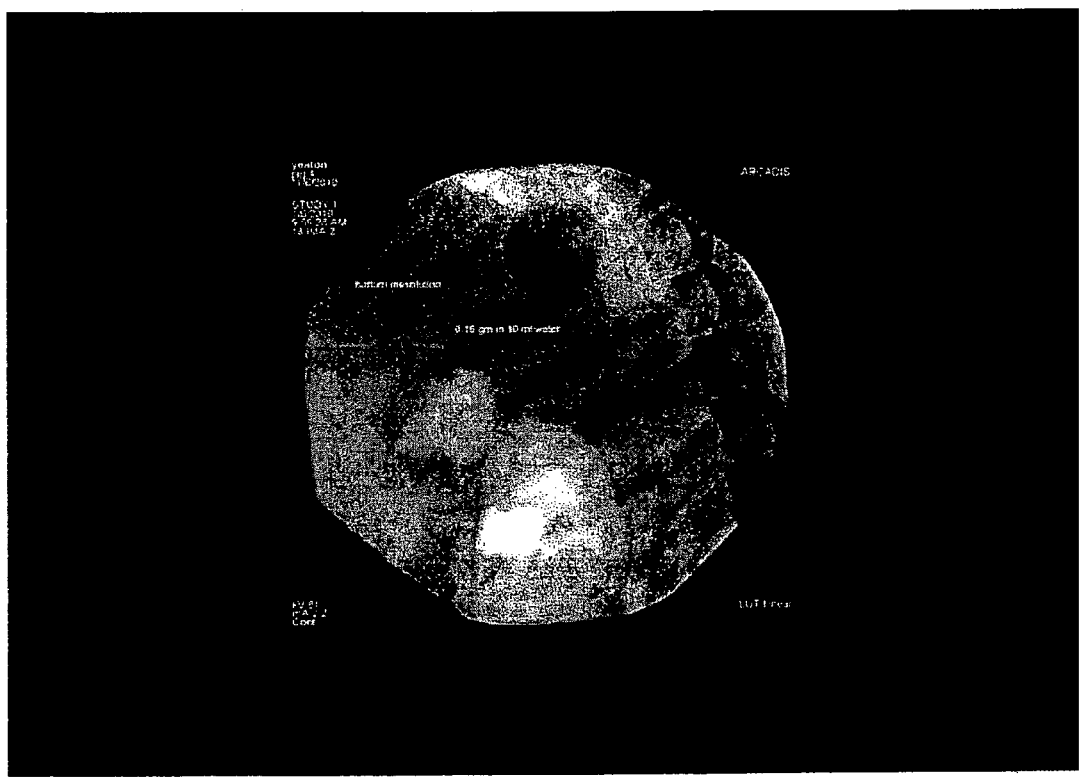
FIG. 17 shows an image of an esophageal balloon comprising a barium sulfate solution admixed at a concentration of 0.16 g barium sulfate in 20 ml of sterile $H_2O$.

FIG. 17 shows an even more opaque X-Ray image of the esophageal balloon, comprising a barium sulfate solution admixed at a concentration of 0.16 g barium sulfate in 20 ml of sterile $H_2O$.

Figure 18:
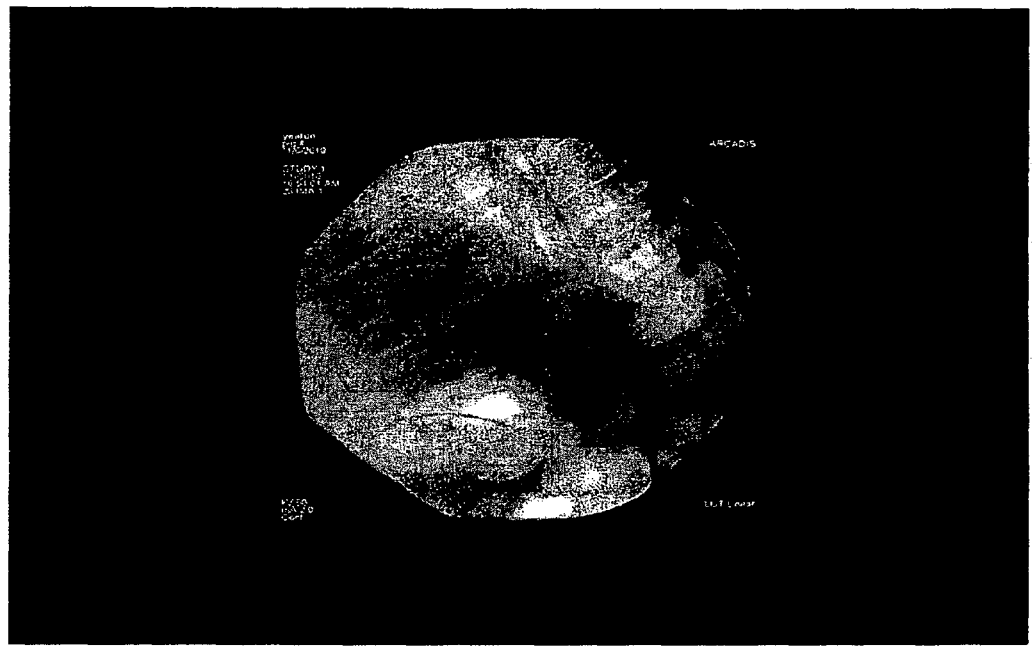
FIG. 18 shows an image of a balloon illuminated with a solution of barium sulfate in sterile $H_2O$.

FIG. 18 shows an X-Ray image of a balloon illuminated with a very low concentration solution of barium sulfate in sterile $H_2O$. The balloon is visible as an outline and features behind the balloon are clearly visible.

Figure 19:
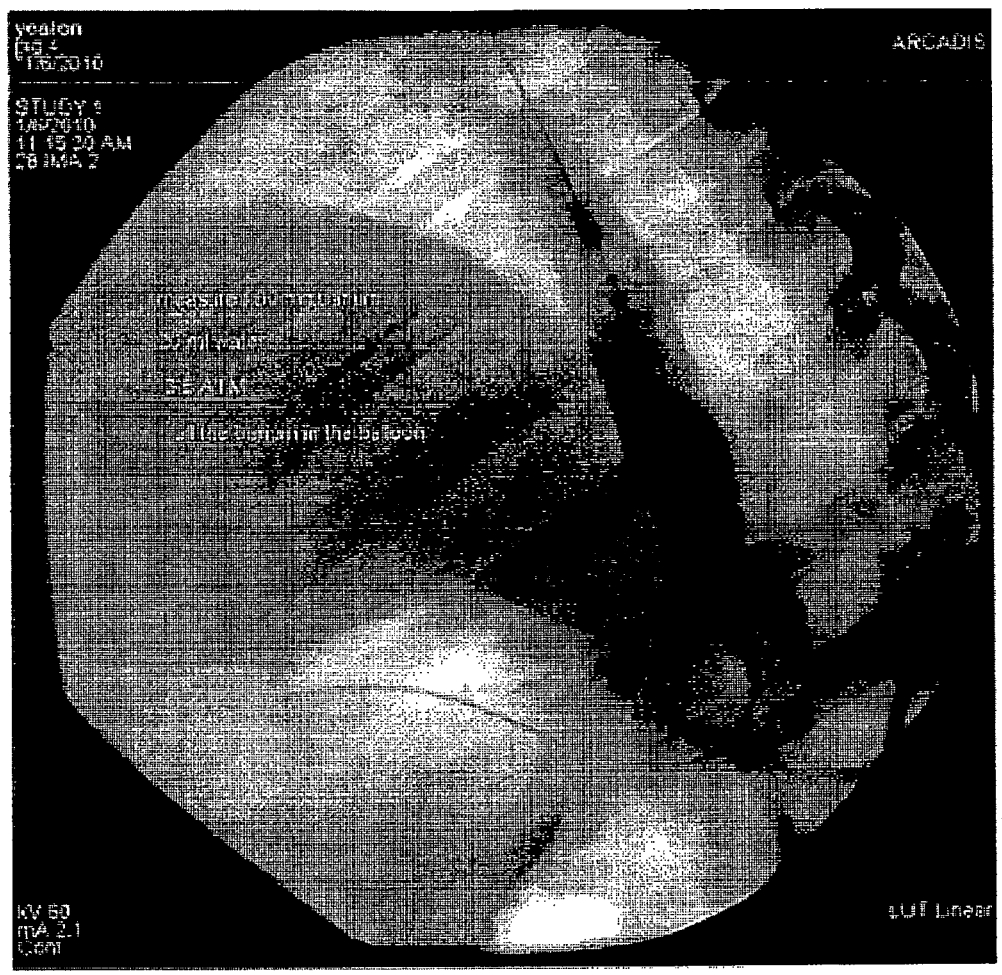
FIG. 19 shows an image of a balloon comprising a barium sulfate solution admixed at a concentration of 60 µg barium sulfate in 20 ml of sterile $H_2O$. The opacity enhancing material is added in an amount large enough to allow an operator to see the balloon clearly but small enough to allow the operator to see the anatomy through the balloon.

FIG. 19 shows an X-Ray image of the same balloon comprising an intermediate barium sulfate solution admixed at a concentration of 60 mg barium sulfate in 20 ml of sterile H20. The image of the balloon is more intense, but feature behind the balloon are still visible.

Figure 20:
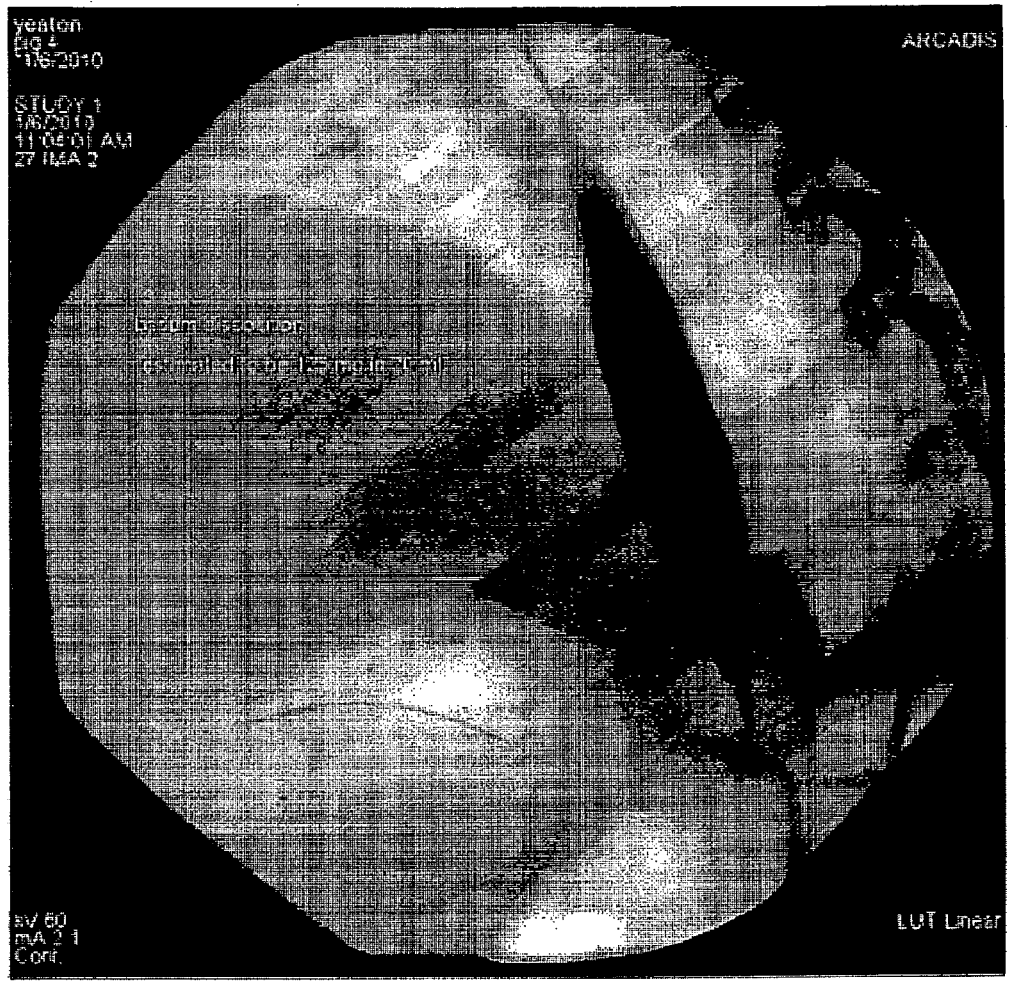
FIG. 20 shows an image of a balloon comprising a barium sulfate solution admixed at a concentration of about 125 mg barium sulfate in 20 ml of sterile $H_2O$.

In FIG. 20, the X-Ray image of the balloon is fully opaque, as features behind the balloon are no longer visible. In this example, the balloon comprises a barium sulfate solution admixed at a concentration of about 125 mg barium sulfate in 20 ml of sterile $H_2O$.

The above description is for the purpose of teaching the person of ordinary skill in the art how to practice the present invention, and it is not intended to detail all those obvious modifications and variations of it which will become apparent to the skilled worker upon reading the description. It is intended however, that all such obvious modifications and variations be included within the scope of the present invention, which is defined by the following claims. The claims are intended to cover the mentioned components and steps in any sequence which is effective to meet the objectives there intended, unless the context specifically indicates the contrary.

What is claimed is:

1. A mixing device comprising a mixing chamber having a first port for connecting to a liquid delivery device, a second port for connecting to a catheter, and an opacity enhancing material inside the chamber,
    wherein the opacity enhancing substance is disposed in a structure configured for placement inside the mixing chamber via a third port on the mixing chamber so that the opacity enhancing substance can become suspended, dissolved or diluted with a liquid received from the first port to form an opacity enhancing liquid.

2. The mixing device of claim 1, wherein the catheter further comprises a balloon at the distal end, wherein the balloon is in fluid communication with the mixing chamber through a conduit.

3. The mixing device of claim 1, wherein the opacity enhancing substance is selected from the group consisting of iodine compounds, barium sulfate, barium iridium, iron particles, tungsten, fluorescent dyes, gadolinium, and microbubbles.

4. The mixing device of claim 1, wherein the catheter is selected from the group consisting of balloon catheters, vascular catheters, cardiac catheters, arterial catheters, venous catheters, neurovascular catheters, intestinal catheters, esophageal catheters, urinary catheters, and Foley catheters.

5. The mixing device of claim 1, wherein the opacity enhancing substance is in a dried, semi-dried or liquid form.

6. The mixing device of claim 1, wherein the mixing chamber further comprises a membrane or screen that separate the mixing chamber into two or more sections.

7. The mixing device of claim 1, wherein the structure configured for placement inside the mixing chamber is a removable and replaceable cartridge.

8. The mixing device of claim 1, wherein the opacity enhancing material is contained in a packet.

9. The mixing device of claim 1, wherein the opacity enhancing material is contained in a tablet.

10. The mixing device of claim 1, wherein the mixing chamber is configured to create a turbulent flow to mix the opacity enhancing substance with the liquid.

* * * * *

UNITED STATES PATENT AND TRADEMARK OFFICE
CERTIFICATE OF CORRECTION

Page 1 of 3

PATENT NO. : 8,706,198 B2
APPLICATION NO. : 13/173414
DATED : April 22, 2014
INVENTOR(S) : Eric K. Mangiardi It is certified that error appears in the above-identified patent and that said Letters Patent is hereby corrected as shown below:

In the Specification

Figure 21B:
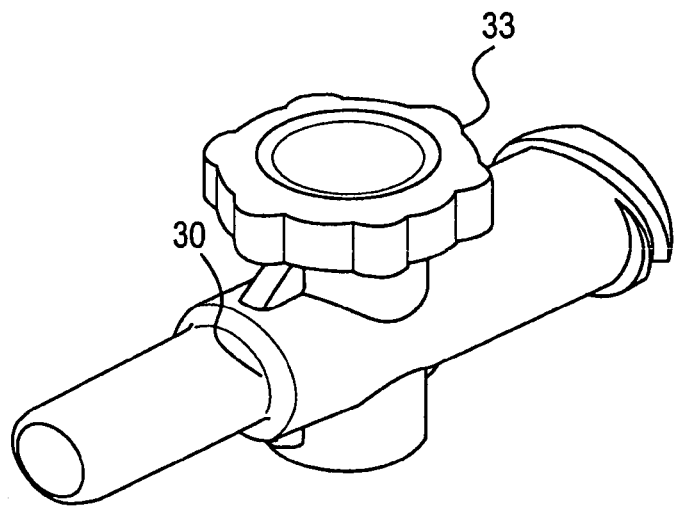
Figure 22A:
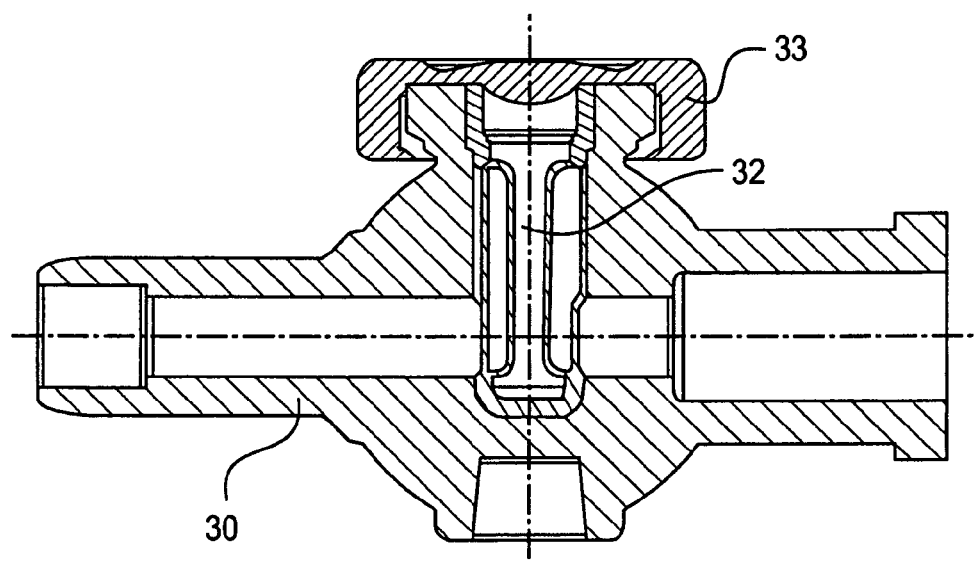
FIG. 22 shows a horizontal longitudinal cut-away view (A) and a transverse cut-away view (B) through the mixing chamber of the device of FIG. 21.
Figure 22B:
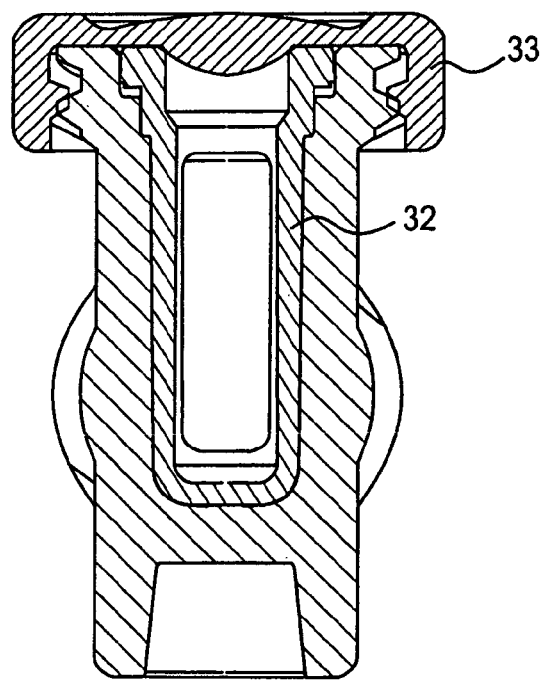
Figure 23A:
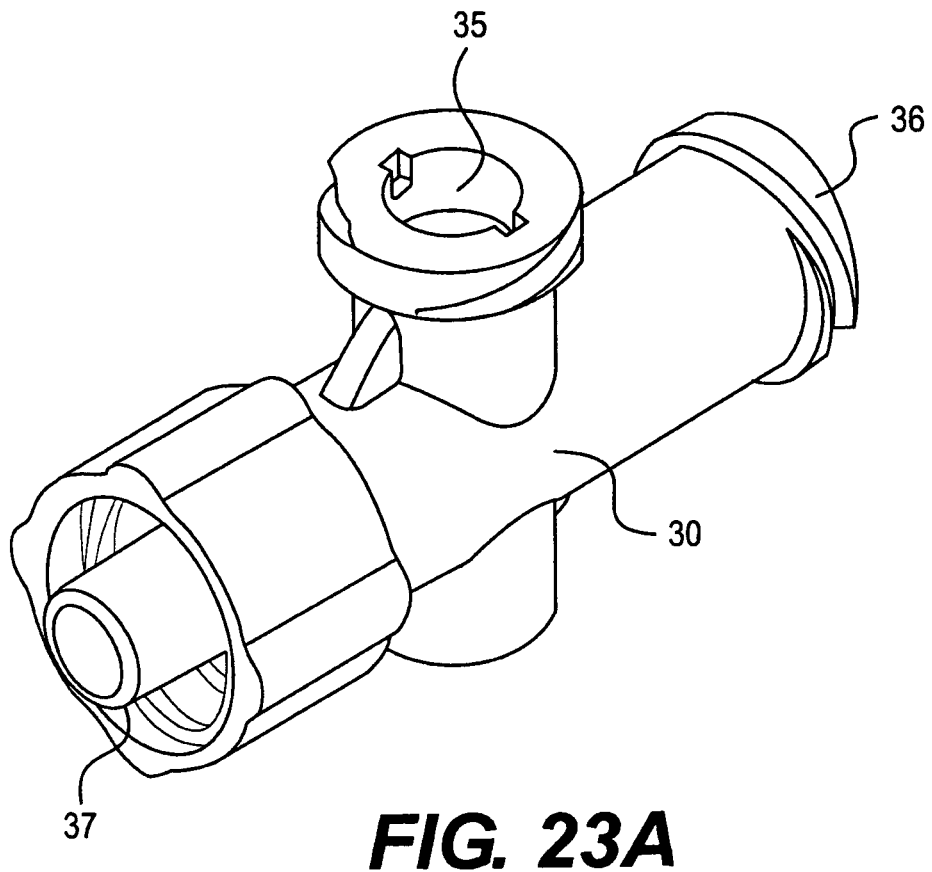
FIG. 23 shows alternate perspective views (A & B) of a mixing chamber of the present invention comprising a female Luer lock receptacle at one end and a male Luer lock fitting at the other end, with a central receptacle for inserting a cylinder containing the opacity substance into the mixing chamber.
Figure 23B:
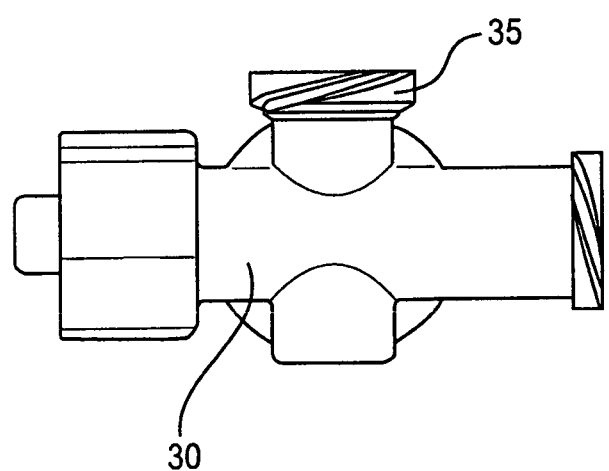
Figure 25A:
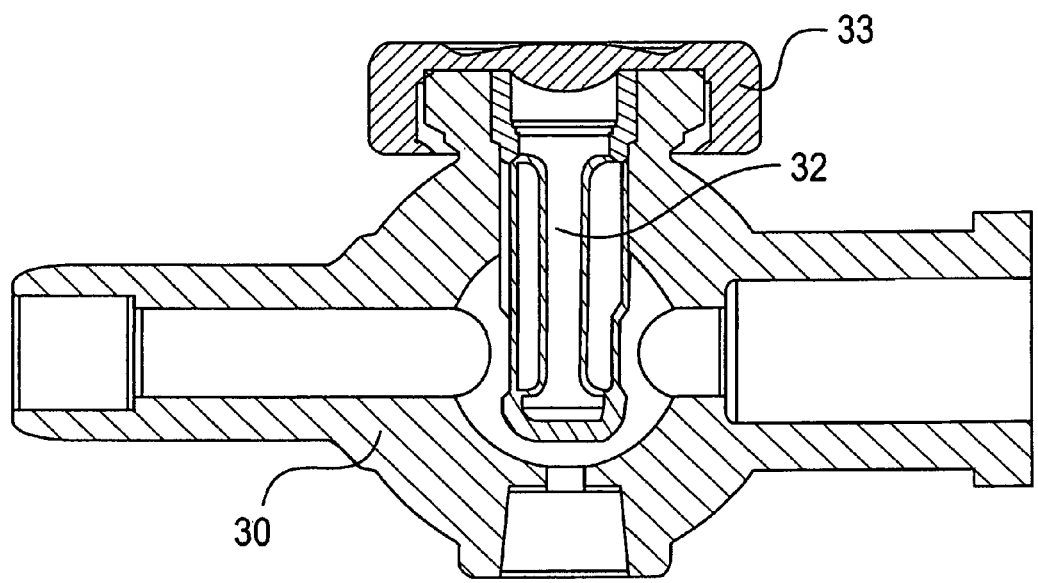
FIG. 25 shows a horizontal longitudinal cut-away view (A) and a transverse cut-away view (B) through the mixing chamber of the device of FIG. 24.
Figure 25B:
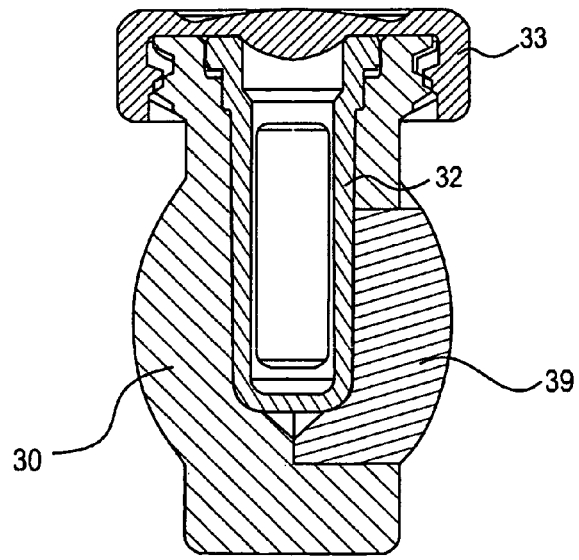

Column 3, line 40: after "mixing," delete "obundboc" and insert --chamber--;

Column 4, line 6: delete "FIG. 21" and insert --FIGS. 21A and 21B--;

Column 4, line 7: after "view," delete "(A)" and insert --FIG. 21A--;

Column 4, line 10: after "device," delete "(B)" and insert --FIG. 21B--;

Column 4, line 11: delete "FIG. 22" and insert --FIGS. 22A and 22B--;

Column 4, line 11: after "view," delete "(A)" and insert --FIG. 22A--;

Column 4, line 12: after "view," delete "(B)" and insert --FIG. 22B--;

Column 4, line 13: after "FIG.," delete "(21)" and insert --FIGS. 21A--;

Column 4, line 14: delete "FIG. 23" and insert --FIGS. 23A and 23B--;

Column 4, line 14: after "views," delete "(A&B)";

Column 4, line 22: delete "FIG. 25" and insert --FIGS. 25A and 25B--;

Column 4, line 22: after "view," delete "(A)" and insert --FIG. 25A--;

Column 4, line 23: after "view," delete "(B)" and insert --FIG. 25B--;

Column 4, line 25: after "bottom," delete "(A & B)" and insert --(panels A & B)--;

Column 4, line 25: after "bottom," delete "(A & B)" and insert --(panels A & B)--;

Column 4, line 25: after "side," delete "(C)" and insert --(panel C)--;

Signed and Sealed this
Seventh Day of October, 2014

Michelle K. Lee
*Deputy Director of the United States Patent and Trademark Office*

CERTIFICATE OF CORRECTION (continued)
U.S. Pat. No. 8,706,198 B2

Figure 26:
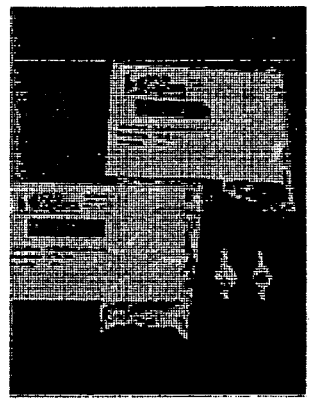
FIG. 26 shows top and bottom (A and B) and side (C) alternate perspective views of a mixing chamber of the present invention comprising a female Luer receptacle at one end and a male Luer fitting at the other end with a central receptacle for introducing the opacity substance into the mixing chamber.
Figure 26:
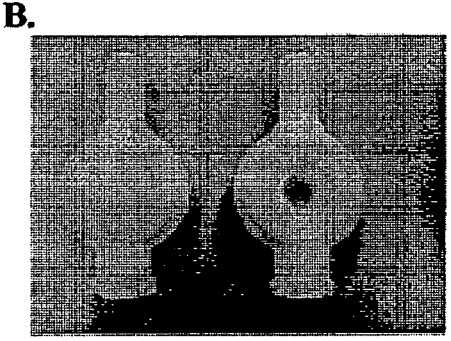
Figure 26:
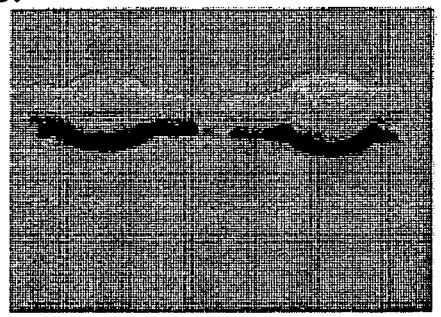
Figure 27:
FIG. 27 shows additional perspective views of the mixing chamber of FIG. 26. (A & B) show the bottom of the device and the outer surface of the cap that snaps into the opening of the central receptacle. (C) shows the top of the device and the inner surface of the cap. (D) is a view of the top of the device showing the central receptacle. (E) is a view of the inner surface of the cap. (F) shows the cap affixed into the central receptacle.
Figure 27:
Figure 27:
Figure 27:
Figure 27:
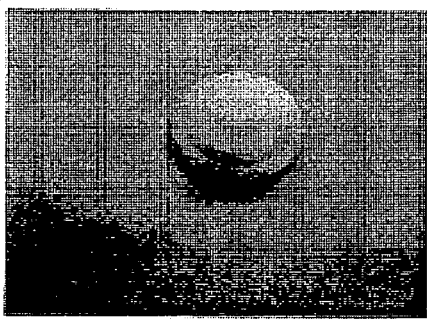
Figure 27:
Figure 28:
FIG. 28 shows alternate perspective views (A-E) of the mixing chamber of FIG. 23 comprising a female Luer lock receptacle at one end and a male Luer lock fitting at the other end, with a central receptacle for inserting a cylinder containing the opacity substance into the mixing chamber.
Figure 28:
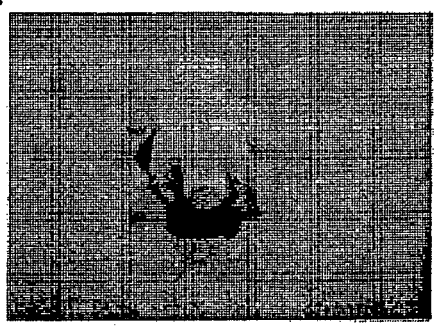
Figure 28:
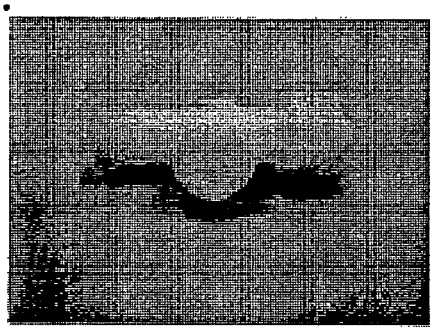
Figure 28:
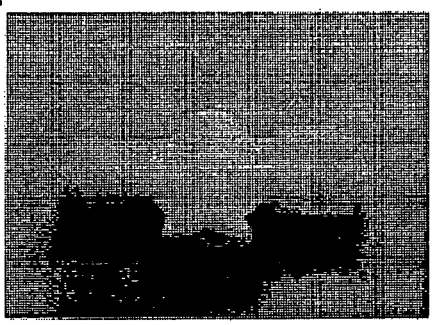
Figure 28:
Figure 29:
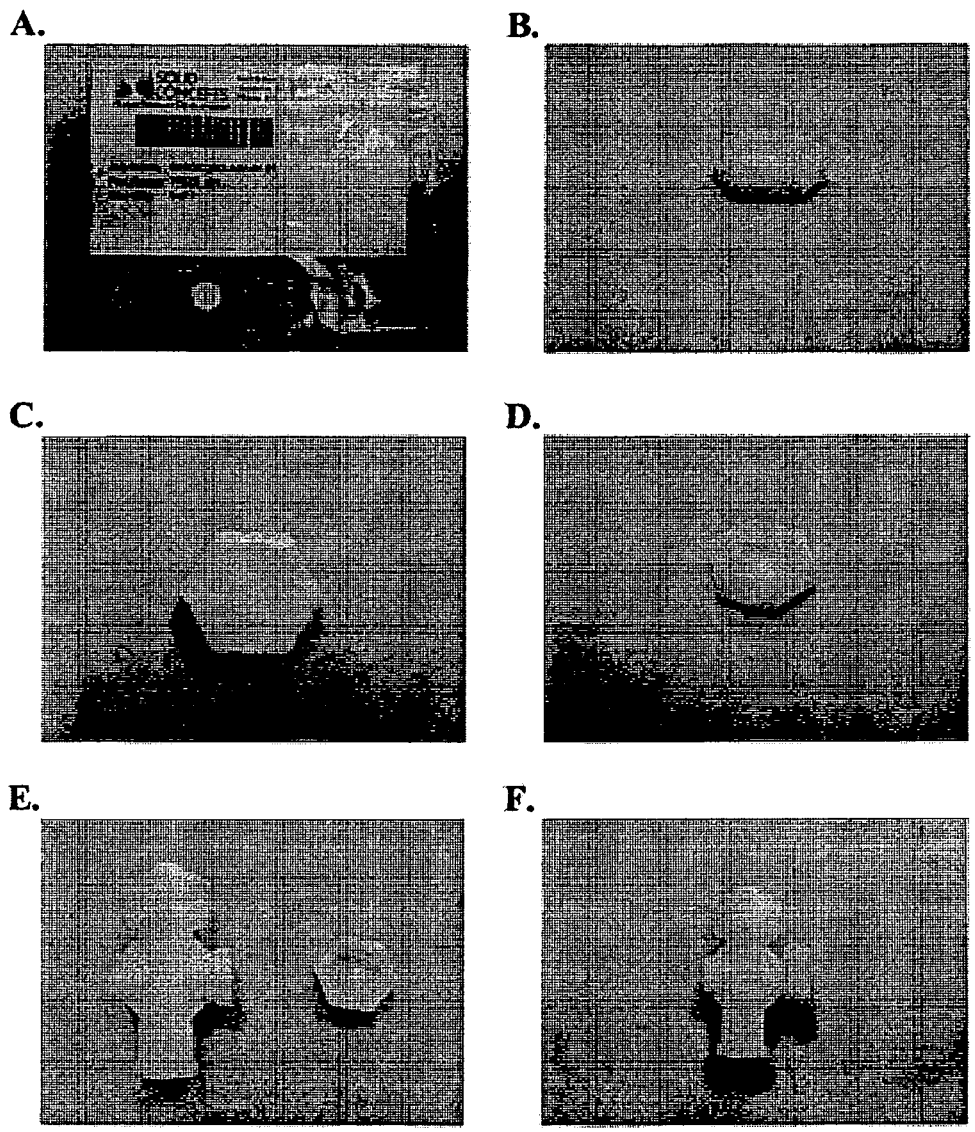
FIG. 29 shows alternate perspective views of the cap for the device of FIG. 28. (A & C) show the top surface of the cap. (B) shows a perspective view of the cap from the side. (D) shows the interior surface of the cap. (E) is a perspective view of the mixing chamber device and the cap. (F) depicts the cap affixed to the mixing chamber.
Figure 30:
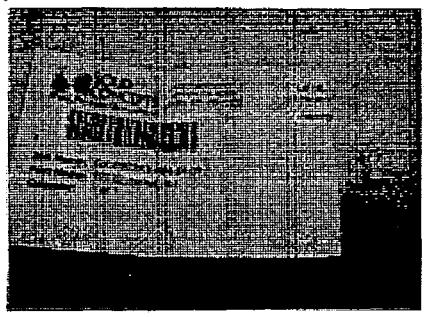
FIGS. 30A-C show perspective views of a cylinder for containing the opacity substance that can be inserted into the central receptacle of a mixing chamber device of the present invention.
Figure 30:
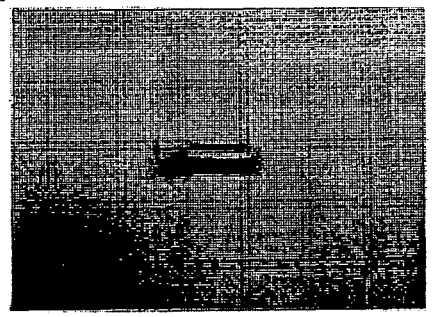
Figure 30:
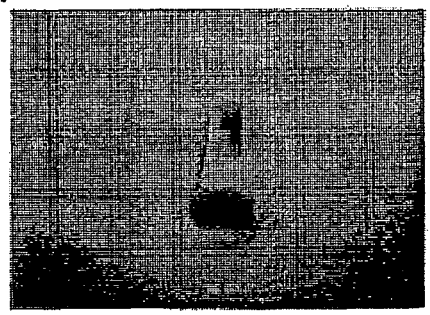
Figure 31:
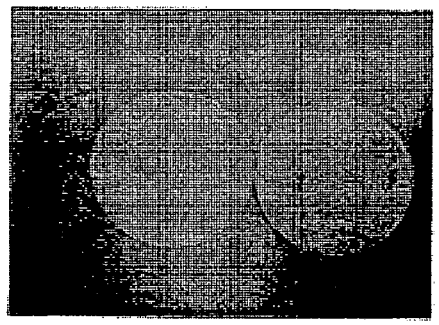
FIGS. 31A-C depict exemplary mesh/screen material that is incorporated into cylinders and/or mixing chambers of the present invention for retaining the opacity substance and/or aiding in the admixture of the opacity substance with the liquid to form the opacity solution.
Figure 31:
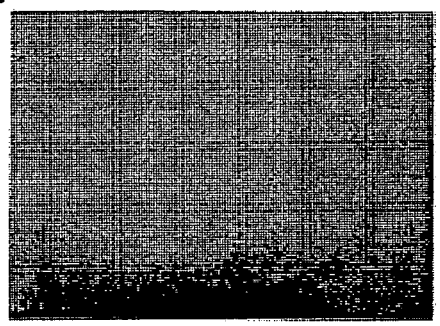
Figure 31:
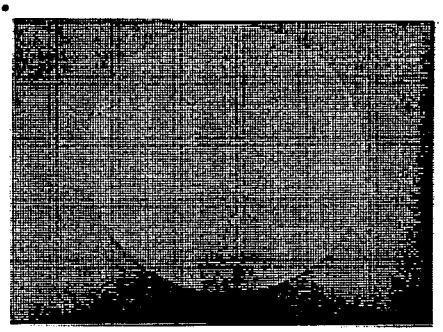

Column 4, line 32: after "FIG. 26." delete "(A & B)" and insert --(panels A & B)--;

Column 4, line 34: after "receptacle." delete "(C)" and insert --(panel C)--;

Column 4, line 35: after "cap." delete "(D)" and insert --(panel D)--;

Column 4, line 36: after "receptacle." delete "(E)" and insert --(panel E)--;

Column 4, line 37: after "cap." delete "(F)" and insert --(panel F)--;

Column 4, line 39: after "views," delete "(A-E)" and insert --(panels A-E)--;

Column 4, line 40: delete "(FIG. 23)" and insert --(FIG. 23A)--;

Column 4, line 45: after "FIG 28." delete "(A & C)" and insert --(panels A & C)--;

Column 4, line 45: after "cap." delete "(B)" and insert --(panel B)--;

Column 4, line 46: after "side." delete "(D)" and insert --(panel D)--;

Column 4, line 47: after "cap." delete "(E)" and insert --(panel E)--;

Column 4, line 48: after "cap." delete "(F)" and insert --(panel F)--;

Column 4, line 50: delete "FIGS. 30A-C" and insert --FIG. 30 (panels A-C)--;

Column 4, line 54: delete "FIGS. 31A-C" and insert --FIG. 31 (panels A-C)--;

Column 9, line 36: delete "FIGS. 14A-B" and insert --FIGS. 14A and 14B--;

Column 9, line 36: after "view," delete "(A)" and insert --(FIG. 14A)--;

Column 9, line 36: after "view," delete "(B)" and insert --(FIG. 14B)--;

Column 9, line 48: delete "FIG. 21 depicts" and insert --FIGS. 21A and 21B depict--;

Column 9, line 60: after "substance." delete "Perspective view (B)" and insert --(FIG. 21B)--;

Column 9, line 66: after "depicted in," delete "FIG. 30A-C" and insert --FIG. 30 (panels A-C)--;

Column 9, line 67: after "depicted in," delete "FIG. 31A-C" and insert --FIG. 31 (panels A-C)--;

Column 10, line 5: after "embodiment," delete "FIG. 23 shows" and insert --FIGS. 23A and 23B show--;

Column 10, line 5: after "shows," delete "alternate perspective views (A & B) of";

Column 10, line 10: after "chamber 30." delete "FIGS. 28 A-E" and insert --FIG. 28 (panels A-E)--;

Column 10, line 12: delete "FIGS. 29 A-E" and insert --FIG. 29 (panels A-E)--;

Column 10, line 16: after "depicted in," delete "FIG. 30 A-c" and insert --FIG. 30 (panels A-C)--;

Column 10, line 17: after "depicted in," delete "FIG. 31 A-C" and insert --FIG. 31 (panels A-C)--.